United States Patent
Eckerdal

(10) Patent No.: US 8,170,691 B2
(45) Date of Patent: May 1, 2012

(54) MEDICAL IMPLANTABLE LEAD

(75) Inventor: Johan Eckerdal, Knivsta (SE)

(73) Assignee: St. Jude Medical AB, Jarfalla (SE)

( * ) Notice: Subject to any disclaimer, the term of this patent is extended or adjusted under 35 U.S.C. 154(b) by 431 days.

(21) Appl. No.: 12/597,768

(22) PCT Filed: Apr. 27, 2007

(86) PCT No.: PCT/SE2007/000412
§ 371 (c)(1),
(2), (4) Date: Oct. 27, 2009

(87) PCT Pub. No.: WO2008/133553
PCT Pub. Date: Nov. 6, 2008

(65) Prior Publication Data
US 2010/0137957 A1   Jun. 3, 2010

(51) Int. Cl.
*A61N 1/18* (2006.01)
(52) U.S. Cl. ........................ 607/127; 600/373
(58) Field of Classification Search .................. 607/127; 600/373
See application file for complete search history.

(56) References Cited

U.S. PATENT DOCUMENTS

| 4,953,564 A | * | 9/1990 | Berthelsen ..................... 607/120 |
| 5,456,708 A | | 10/1995 | Doan et al. |
| 5,593,433 A | | 1/1997 | Spehr et al. |
| 5,776,178 A | | 7/1998 | Pohndorf et al. |
| 6,038,463 A | * | 3/2000 | Laske et al. ................... 600/374 |
| 6,129,751 A | | 10/2000 | Lucchesi et al. |
| 7,092,766 B1 | | 8/2006 | Salys et al. |

FOREIGN PATENT DOCUMENTS

WO  WO 2007/123433  11/2007

\* cited by examiner

*Primary Examiner* — Carl H Layno
*Assistant Examiner* — Natasha Patel
(74) *Attorney, Agent, or Firm* — Schiff Hardin LLP

(57) ABSTRACT

A medical implantable lead has a proximal end and a distal end, a biostable and biocompatible polymeric header, which is arranged at the distal end and has a first tubular portion, a helical fixation element located within the first tubular portion and being extendable from a distal end of the header, and a radiopaque ring. The header further has a second tubular portion, which is arranged coaxially of the first tubular portion and is attached to the first tubular portion at a distal end of the second tubular portion, while having a free proximal end. The tubular portions form a circumferential pocket, wherein the first tubular portion extends from the proximal end of the header at least to said distal end of the second tubular portion. The radiopaque ring is arranged around the first tubular portion and is received in the circumferential pocket.

10 Claims, 1 Drawing Sheet

MEDICAL IMPLANTABLE LEAD

BACKGROUND OF THE INVENTION

1. Field of the Invention

The present invention relates to a medical implantable lead having a header arranged at a distal end thereof and a radiopaque ring arranged at the header.

2. Description of the Prior Art

A lead of the type mentioned above typically has a lumen extending between its ends and an electrode extending through the lumen. In order to be able to securely connect the electrode to body tissue a helical fixation element, also called helix, is arranged at the distal end of the electrode. The helix is extendable and retractable within the lumen by means of rotating the helix. The tip of the helix is sharp in order to easily penetrate body tissue. In order to be able to provide good guidance to a user who is going to fasten the helix in the body tissue, a radiopaque ring is applied as close to the distal end of the header as possible. The ring is used as a marker, or position reference, for the position of the helix.

One example of such a lead is disclosed in U.S. Pat. No. 7,092,766, Salys et al. The lead is provided with a collar, which is a radiopaque ring, at the very distal end of the lead. The collar is welded to the header, which extends proximally of the collar. It is a desire, for many reasons including avoiding shatter-noise due to electrical contact between the helix and the metal header, increasing electrode impedance, and providing good properties of interaction with the body tissue, to form the header from a polymer and having such a polymer header define the very distal end portion of the lead. Then it will not be possible to weld the header with the radiopaque ring, but it will be necessary to use an adhesive. Then a question arises regarding how to arrange the radiopaque ring to minimize potential new problems of the adhesive fastening of the ring to the header. Also there is a general question about how to arrange the radiopaque ring at the header close enough to the distal end to maintain a good guide function.

SUMMARY OF THE INVENTION

It is an object of the present invention to provide a lead with a polymeric header and a radiopaque ring arranged at the header.

In accordance with an aspect of the present invention, there is provided a medical implantable lead having a proximal end and a distal end, a header, which is made of a biostable and biocompatible polymer, and which is arranged at the distal end and having a first tubular portion, a helical fixation element located within the first tubular portion and being extendable from a distal end of the header, and a radiopaque ring. The header further has a second tubular portion, which is arranged coaxially of the first tubular portion and is attached to the first tubular portion at a distal end of the second tubular portion, while having a free proximal end, thereby forming a circumferential pocket. The first tubular portion extends from the proximal end of the header at least to the distal end of the second tubular portion, and the radiopaque ring is arranged around the first tubular portion and is received in said circumferential pocket.

Providing the header with a pocket and putting the marker ring therein is a simple solution of mounting the radiopaque ring in a shielded way, and an end portion of the helical fixation element is invisible on fluoroscopy when being inside of the ring, until it is extended from the header. Alternatively, or additionally, the radiopaque ring is used as a position reference in cooperation with a proximal radiopaque movable part, which follows the helix when the helix is extended or retracted. Further, the radiopaque ring is mountable from the proximal end of the header by simply moving it distally along the first tubular portion and into the pocket.

For the purposes of this application, the expression that the helical fixation element is "extendable from the distal end" means that it can be moved distally out of the distal end. Typically this is obtained by rotating the helical fixation element.

In accordance with an embodiment of the medical implantable lead, it further has a ring electrode, which is arranged at the header and connected to a conductor. The conductor extends between the ring electrode and the proximal end of the lead. The ring electrode is arranged adjacent to the radiopaque ring, and has the same outer diameter as the second tubular portion. Thereby the ring electrode as well as the radiopaque ring is easily mountable onto the header.

In accordance with an embodiment of the medical implantable lead, the ring electrode and the radiopaque ring are welded together. Thereby the mounting is further facilitated and shatter-noise, due to the rings having irregular contact with each other, is avoided.

In accordance with an embodiment of the medical implantable lead, an insulating layer is applied between the radiopaque ring and the ring electrode. The same advantage as by welding is obtained in this embodiment.

In accordance with an embodiment of the medical implantable lead, the ring electrode is arranged at a distance from the radiopaque ring, and has the same outer diameter as the second tubular portion. The lead further has a sleeve enclosing the first tubular portion between said ring electrode and said radiopaque ring and having the same diameter as the second tubular portion. This is an alternative way of arranging the ring electrode.

In accordance with an embodiment of the medical implantable lead, the ring electrode is radiolucent. Thereby, even if the ring electrode is placed adjacent to the radiopaque ring, the radiopaque ring alone provides a distinct position of the helical fixation element.

In accordance with an embodiment of the medical implantable lead, a distal end surface of the header is textured such as to obtain an increased friction towards a biological tissue relative to a smooth surface. This embodiment is, inter alia, advantageous in that it reduces the risk of the header rotation along with the helical fixation element when it is to be extended by rotation thereof. In another embodiment of the lead according to the present invention, the texture is chosen such as to generate an enhanced response from the body tissue, which is engaged with the surface.

These and other aspects, features, and advantages of the invention will be apparent from and elucidated with reference to the embodiments described hereinafter.

DESCRIPTION OF THE PREFERRED EMBODIMENTS

Figure 1:
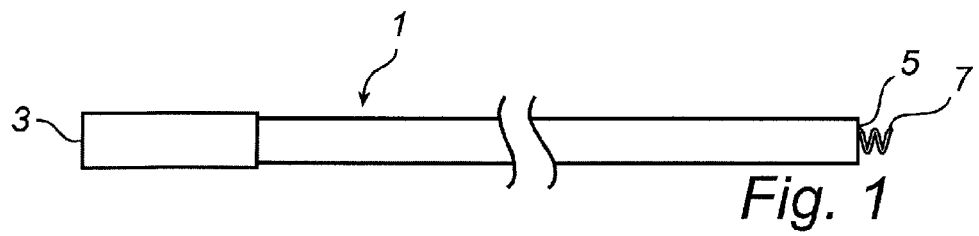
FIG. 1 is a schematic side view of a medical implantable lead.

Referring to FIG. 1 a medical implantable lead 1 has a proximal end 3 and a distal end 5. At the distal end 5 a helical fixation element 7 is arranged within a lumen 39, see FIG. 2, of the lead 1. The helical fixation element, which below will be referred to as a helix, 7 is extendable from the distal end 5, and retractable into the lumen. In FIG. 1 it is shown in the extended position. The lead shown in FIG. 1 is most schematic but also general figure of a lead. Thus, the description thereof is valid for all embodiments that will be described below. For example the lead 1 is used with a pulse generator, where the distal end 5 thereof is introduced into a cardiac cavity.

Figure 2:
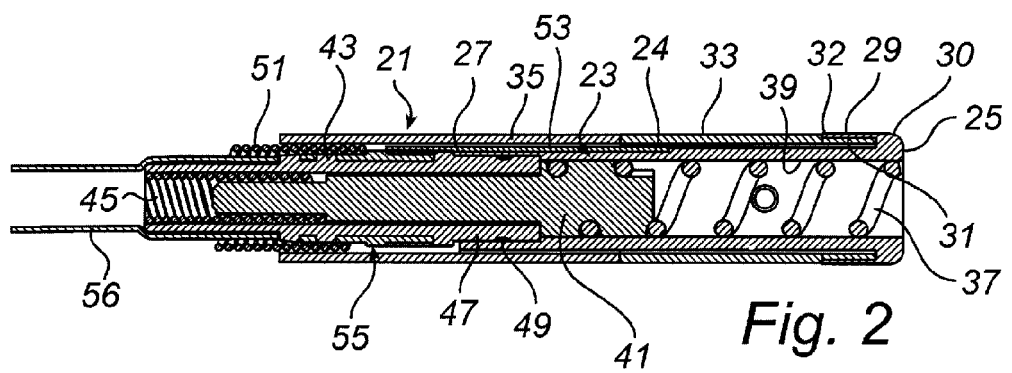
FIGS. 2 and 3 are cross-sectional views of embodiments of leads having different configurations of the elements at the distal end of the lead.

In accordance with a first embodiment of the lead according to the present invention, as shown in FIG. 2, a distal end assembly of the lead 21 comprises a header 23, a radiopaque ring, or marker ring, 31, ring electrode 33, a helix 37, and a shaft 41. The header 23 has a proximal end 27 and a distal end 25, which constitutes the distal end of the lead 1 as well. The header 23 has a first tubular portion 24, reaching between its ends 27, 25, within which the helix 37 is arranged. The helix is attached to the shaft 41, at a distal portion thereof, and the shaft 41 is attached to an inner conductor 45, which extends through a central lumen, defined by an inner insulating tube 56, of the lead 21 to the proximal end of the lead 21. The helix 37 is electrically connected with the inner conductor 45 via the shaft 41. At a proximal end portion thereof the header 23 is attached to a tubular coupling 43, which extends proximally thereof. More particularly, in this embodiment a distal end portion 47 of the coupling 43 reaches into the header 23 and engages therewith. The connection is secured by means of a snap lock arrangement 49 consisting of a circumferential rim on the inner surface of the header 23 and a corresponding circumferential groove on the outer surface of the coupling 43, in which the rim is received. One alternative solution is to apply an adhesive instead. A portion of the shaft 41 extends within a portion of the coupling 43 and is movably supported by the coupling 43, which can be considered as a bearing for the shaft 41.

The inner insulating tube 56 of the lead 21 extends coaxially of the inner conductor 45. At a distal end portion of the inner tube 56 it has been pushed onto and engages with a proximal end portion of the coupling 43.

It should be noted that the form and arrangement of the helix 37, the shaft 41, the inner conductor 45, and the coupling 43, as shown and described in conjunction with FIG. 2, is not central for the invention, but is a mere example of an environment in which the header 23 is used. Thus, the arrangement of the helix, the shaft, etc. can be done according to any known or future arrangement that is applicable in cooperation with the header of this invention, as defined by the appended claims.

According to the first embodiment the header 23 is further provided with a second tubular portion 29 which is arranged coaxially of the first tubular portion 24, and which is attached to the first tubular portion at a distal end 30 of the second tubular portion 29, while having a free proximal end 32, thereby forming a circumferential pocket. Thus, the second tubular portion 29 can be seen as a circular tongue protruding proximally from the attachment at the distal end 30 of the second tubular portion 24. In this embodiment the first tubular portion 24 extends from the proximal end 27 of the header 23 to the distal end 30 of the second tubular portion 29. Thus, the distal ends 25, 30 of the first and second portions 24, 29 coincide. The longitudinal length of the second tubular portion 29 is but a small fraction of the length of the first tubular portion 24. The marker ring 31 is arranged around the first tubular portion 24 and is received in the circumferential pocket. Here the marker ring 31 entirely fills the pocket. In other words the length, along the lead 21, of the marker ring 31 corresponds with the depth of the pocket, and the thickness, radially of the lead 21, of the marker ring 31 corresponds with the width of the pocket. When mounting the marker ring 31 it is slipped onto the first tubular portion 24 of the header 23 from the proximal end 25 thereof, along the first tubular portion 24 and into the pocket between the inner wall of the second tubular portion 29 and the outer wall of the first tubular portion 24.

The ring electrode 33 is arranged adjacent to the marker ring 31, and a thin insulating layer is applied between the marker ring 31 and the ring electrode 33. Alternatively, the marker ring 31 and the ring electrode 33 have been welded together before mounting on the header 23. The ring electrode 33 is electrically connected with an outer conductor 51, which extends between the ring electrode 33 and the proximal end of the lead 21. The outer conductor 51 is a coil conductor and is arranged outside and coaxially of the inner insulating tube 56. The ring electrode 33 is connected with the outer conductor 51 via a conducting strip 53, which is arranged in a groove at the outer surface of the inner tubular portion 24 of the header 23, and a ring shaped interface element 55. The interface element 55 is mounted on the coupling 43. Thus, the strip 53 is attached to the interface element 55, while the outer conductor 51 is attached to the interface element.

An outer insulating tube 35 has been slipped over the outer conductor 51 into abutment against the distal end surface of the ring electrode. The outer diameters of the outer insulating tube 35, the ring electrode 33 and the second tubular portion 29 of the header 23 are the same, and thereby a smooth outer surface of the lead 21 has been achieved.

When the helix 37 is in the fully retracted position, the tip of the helix 37 is preferably, but not necessarily, positioned in the marker ring 31 and is thereby invisible to an operator, who uses some kind of radioscopy to see the lead 21, and in particular the helix 37, when mounting it within a human body. When the helix 37 is extended distally, out of the header 23, typically performed by the operator rotating the inner conductor 45 at the proximal end thereof, the tip of the helix 37 becomes visible to the operator distally of the marker ring 31. As mentioned above, the marker ring 31 is alternatively, or additionally, used as a position reference for a movable radiopaque part of the lead. For instance, such a movable part is the shaft 41, and more particularly the distal end thereof, where the operator monitors the distance between that distal end and the marker ring 31.

Figure 3:
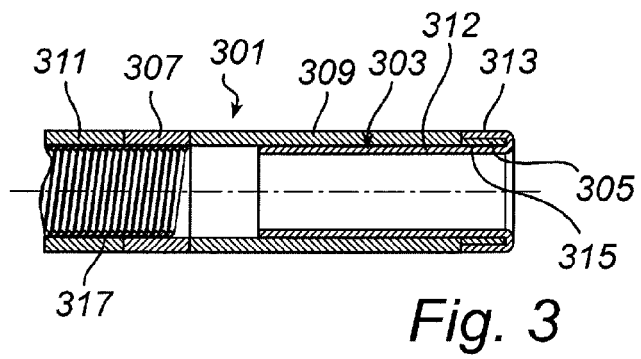

In accordance with a second embodiment of the lead according to the present invention, as shown in FIG. 3, the ring electrode 307 has been positioned differently than in the first embodiment. As in the first embodiment, the lead 301 includes a header 303, which has first and second tubular portions 312 and 313, which form a pocket 315, wherein a marker ring 305 has been received. However, adjacent to the marker ring 305 a header sleeve 309 is arranged. The header sleeve 309 encompasses the first tubular portion 312 proximally of the marker ring 305, and protrudes a bit proximally of the header 303. The ring electrode follows proximally of the header sleeve 309, and an outer insulating tube 311 engages with the proximal end of the ring electrode 307. In this embodiment an outer coil conductor 317 has been welded directly to the ring electrode 307.

In all embodiments the header is made of a biostable and biocompatible polymer. An example of a useful, and preferred, polymeric material is PEEK, i.e. Polyetheretherketone. Other useful polymeric materials are polysulfone and PMMA (Polymethylmethacrylate). The radiopaque ring, or marker ring, is preferably made of Ta (Tantalum), while the ring electrode preferably is made of a radiolucent material, such as TiN (Titanium Nitride), or of a TiN coated Ti substrate. An alternative to Ta for the marker ring is PtIr (Platinum Iridium).

Figure 4:
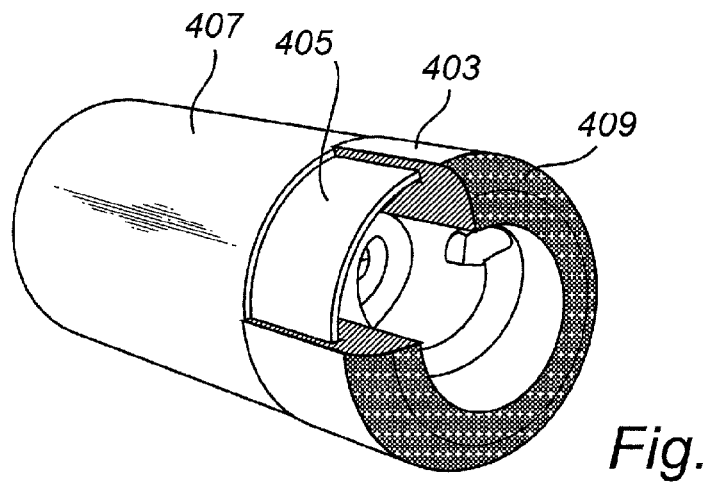
FIG. 4 is a perspective view of a distal end portion of an embodiment of the lead.

By making the header of a polymer, new possibilities of providing the very distal end thereof with a particular surface texture, that has advantageous additional properties compared to a general smooth surface, arise. Thus, referring to FIG. 4, which shows a header portion with the header 403, the marker ring 405, and the ring electrode 407, the end surface, or front surface, 409 of the header 403 is textured. This end surface 409 has the function of cooperating with body tissue. For example, in a pacemaker application, the end surface is engaging with cardiac tissue, where problems of for example fibrosis, inflammation, and high pace thresholds are common. Such problems are decreasable by providing the end surface 409 with an appropriate texture, which is enabled in accordance with this invention. A texture can also be applied in order to increase the friction against the tissue, thereby preventing the header 403 from being brought along in the rotation when the helix is rotated.

Above, one embodiment of the medical implantable lead according to the present invention has been described. This should be seen as merely a non-limiting example. As understood by a skilled person, many modifications and alternative embodiments are possible within the scope of the invention.

Although modifications and changes may be suggested by those skilled in the art, it is the intention of the inventor to embody within the patent warranted heron all changes and modifications as reasonably and properly come within the scope of his contribution to the art.

I claim:

1. An implantable medical lead comprising:
   a lead body adapted for in vivo implantation in a living subject, said lead body comprising a proximal end configured for electrical and mechanical connection to a therapy device, and a distal end configured for in vivo interaction with tissue;
   a header at said distal end, said header being comprised of a biostable and biocompatible polymer, said header comprising a first tubular portion, a helical fixation element located within said first tubular portion and being extendable from said distal end to interact with said tissue, and a radiopaque ring;
   said header further comprising a second tubular portion at said distal end located coaxially with respect to said first tubular portion, said second tubular portion having a second tubular portion distal end and a free proximal end, said second tubular portion being connected to said first tubular portion at said second tubular portion distal end to form a circumferential pocket;
   said header having a header proximal end and said first tubular portion extending from said header proximal end at least to said second tubular portion distal end; and
   said radiopaque ring extending around said first tubular portion and being received in said circumferential pocket.

2. A medical implantable lead as claimed in claim 1 wherein said header has a distal end surface that is textured to produce increased friction with respect to said tissue, compared to a smooth surface.

3. A medical implantable lead as claimed in claim 1 wherein said header has a distal end surface that is textured to obtain an enhanced response from tissue interacting with said surface.

4. A medical implantable lead as claimed in claim 1 comprising a ring electrode at said header and a conductor connected to said ring electrode and extending through said lead body from said ring electrode to said proximal end of said lead body, said ring electrode being located at a distance from said radiopaque ring and having a same outer diameter as said second tubular portion, and a sleeve enclosing said first tubular portion between said ring electrode and said radiopaque ring, said sleeve having a same diameter as said second tubular portion.

5. A medical implantable lead as claimed in claim 4 wherein said ring electrode is radiolucent.

6. A medical implantable lead as claimed in claim 1 comprising a ring electrode at said header, a conductor connected to said ring electrode and extending through said lead body from said ring electrode to said proximal end of said lead body, said ring electrode being located adjacent to said radiopaque ring and having a same outer diameter as said second tubular portion.

7. A medical implantable lead as claimed in claim 6 comprising exterior insulating tubing extending coaxially with respect to said first tubular portion and enclosing a portion of said first tubular portion, said insulating tubing having an outer diameter equal to an outer diameter of said second tubular portion and abutting against said ring electrode.

8. A medical implantable lead as claimed in claim 6 wherein said ring electrode is radiolucent.

9. A medical implantable lead as claimed in claim 6 wherein said ring electrode and said radiopaque electrode are welded together.

10. A medical implantable lead as claimed in claim 9 comprising an insulating layer between said radiopaque ring and ring electrode.

* * * * *